United States Patent [19]
Kreider

[11] 3,959,275
[45] May 25, 1976

[54] FUSED RING N-[1-(3-CYANO-3,3-DIPHENYLPROPYL)-4-PHENYLPIPERIDINE-4-CARBONYLOXY]IMIDES

[75] Inventor: Eunice M. Kreider, Chicago, Ill.
[73] Assignee: G. D. Searle & Co., Chicago, Ill.
[22] Filed: May 28, 1974
[21] Appl. No.: 473,750

Related U.S. Application Data
[62] Division of Ser. No. 208,442, Dec. 15, 1971, Pat. No. 3,847,923.

[30] Foreign Application Priority Data
Dec. 16, 1970 United Kingdom............. 59686/70

[52] U.S. Cl............................ 260/248 AS; 424/249; 260/293.71; 260/293.69; 260/250 Q; 260/293.8
[51] Int. Cl.²...................................... C07D 253/08
[58] Field of Search............................ 260/248 AS

[56] References Cited
UNITED STATES PATENTS
3,847,923   11/1974   Kreider................ 260/248

Primary Examiner—John M. Ford
Attorney, Agent, or Firm—John J. McDonnell

[57] ABSTRACT

Preparation of the subject compounds by reaction of 1-(3-cyano-3,3-diphenylpropyl)-4-phenylpiperidine-4-carboxylic acid with an N-hydroxy compound of the type HO—N Q wherein

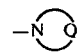

represents an optionally substituted monocyclic- or fused polycylic-heterocyclic radical containing at least one carbonyl function adjacent the nitrogen atom, in the presence of a suitable dehydrating agent, and their useful biological properties, including analgesic and especially potent antidiarrheal activity are disclosed.

1 Claim, No Drawings

FUSED RING N-[1-(3-CYANO-3,3-DIPHENYLPROPYL)-4-PHENYLPIPERIDINE-4-CARBONYLOXY]IMIDES

This is a division of application Ser. No. 208,442, filed Dec. 15, 1971, now U.S. Pat. No. 3,847,923, issued Nov. 11, 1974.

The present invention relates to N-[1-(3-cyano-3,3-diphenylpropyl)-4-phenylpiperidine-4-carbonyloxy]imides and related compounds of the following structural formula wherein

represents an optionally substituted monocyclic- or fused polycyclic- heterocyclic radical containing at least one carbonyl function adjacent the nitrogen atom.

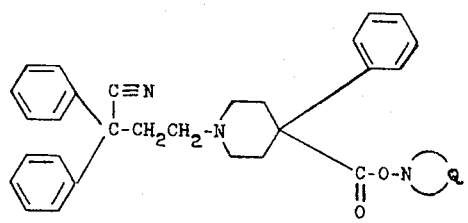

(I)

Illustrative of the radicals represented by —N Q are succinimido, glutarimido, phthalimido, endo-5-norbornene-2,3-dicarboximide, 3,4-dihydro-4-oxo-1,2,3-benzotriazin-3-yl, and 3,4-dihydro-4-oxo-quinazolin-3-yl. The quinazolinyl radical can be optionally substituted, for example, with a bromine atom at positions 5 through 7, and with a methyl or phenyl radical at the 2-position. Additional radicals represented by —N Q include 3,4-dihydro-3-oxo-2H-1,4-benzoxazin-4-yl and 3,4-dihydro-3-oxo-2H-1,4-benzothiazin-4-yl and the corresponding 2-(o-chlorobenzylidene), 6-chloro, 6-chloro-2-methyl, 6-bromo, 2-ethyl, 2-methyl, 2,2-dimethyl, 2-carboxymethyl and 2-carboxymethyl-6-methyl derivatives; 2-oxoindol-1-yl, optionally containing an oxo, phenyl or benzylidene substituted at the 3-position; 4,5,6,7-tetrahydro-4,6-dioxo-3-methylisothiazolo[5,4-d]-pyrimidin-5-yl; 1,2,3,4-tetrahydro-1,3-dioxoisoquinolin-2-yl; 3-cyano-1,2-dihydro-1-oxoisonquinolin-2-yl; 9,10-dihydro-5,10-dioxo-4-oxa-9-azapyren-9-yl; 3-carboxy-1,2-dihydro-2-oxo-1,8-napthyridin-1-yl; and 4-oxopyridopyrimidin-3-yl radicals, the latter preferably containing a methyl substituent at the 2-position and optionally containing additional methyl groups on the pyridine or pyrimidine portion of the radical. Specific illustrations of such pyridopyrimidin 3-yl radicals are 3,4-dihydro-4-oxo-2,6,8-trimethylpyrido[3,4-d]pyrimidin-3-yl; 2-methyl-4-oxopyrido[3,2-d]pyrimidin-3-yl; and 2-methyl-3,4-dihydro-4-oxo-pyrido[3,2-d]pyrimidin-3-yl.

The compounds of formula (I) can be conveniently prepared by contacting a compound of the general formula

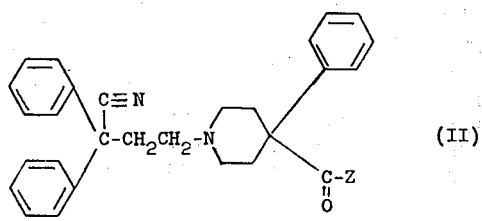

(II)

wherein Z is a chlorine atom or a hydroxy radical, with a compound of the formula

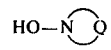

(III)

wherein —N Q is defined as before.

When Z in formula (II) is a hydroxy radical, i.e. when the acid starting material is employed, the reaction is conducted in the presence of a suitable dehydrating agent. Suitable dehydrating agents include aromatic carbodiimides such as diphenylcarbodiimide; and aliphatic carbodiimides such as diethylcarbodiimide and, preferably, dicyclohexylcarbodiimide. Other dehydrating agents which may be suitable include bases such as sodium carbonate and acids such as sulfuric acid, hydrochloric acid and toluenesulfonic acid. Other possible dehydrating agents may include trifluoroacetic anhydride and boron trifluoride etherate. Time, temperature and pressure are not critical factors for the conduct of this reaction; however, the reaction is preferably conducted initially at slightly elevated temperature, e.g. between 40°–60°C., and conveniently at atmospheric pressure. Typical reaction times vary between 3 hours and 3 days and are dependent on the particular temperature and reactants involved. Suitable solvents are non-protic solvents (i.e. solvents containing no acidic hydrogen atoms) which are capable of dissolving the acid of formula (II) at the temperature employed. Such suitable solvents include dimethylformamide, dimethylacetamide, and hexamethylphosphoramide.

When Z in formula (II) is a chlorine atom, i.e. when the starting material is the acid chloride, the reaction is conveniently conducted in the presence of a suitable base. Preferred bases for use in this reaction include tertiary aliphatic or aromatic amines, e.g. N-methylmorpholine, triethylamine, pyridine and picoline. The reaction is conveniently carried out at atmospheric pressure, at a temperature ranging from room temperature to reflux and for a time period of 5 minutes to 24 hours. However, time, temperature and pressure are not critical factors in conducting the reaction. Suitable solvents are non-protic solvents, e.g. dimethylformamide, dimethylacetamide, hexamethylphosphoramide, dimethylsulfoxide, tetrahydrofuran, acetonitrile, benzene and the like.

The starting material of formula (II) wherein Z is a chlorine atom is conveniently prepared from the corresponding acid of formula (II) by reaction with thionyl chloride in an inert solvent such as tetrahydrofuran, optionally in the presence of dimethylformamide. The acid chloride of formula (II) is particularly useful in the form of its hydrohalide salts, especially in the form of its hydrochloride. Said acid chloride is also the starting material of choice when the N-hydroxy compound of formula (III) contains reactive substituents, e.g. carboxymethyl or carboxy groups. Specific examples of N-hydroxy starting materials which contain such substituents and which are consequently most advantageously utilized in the reaction with the acid chloride of formula (II) include 2H-1,4-benzothiazine-2-acetic acid, 6-methyl-2H-1,4-benzothiazine-2-acetic acid and 1,2-dihydro-1-hydroxy-2-oxo-1,8-naphthyridine-3-carboxylic acid.

Equivalent to the free bases of formula (I) for the purposes of this invention are the non-toxic pharmaceutically acceptable acid addition salts thereof. Such salts include those derived from inorganic acids such as hydrochloric, hydrobromic, hydriodic sulfuric, phosphoric, nitric, and sulfamic; and from organic acids such as acetic, citric, lactic, maleic, malic, succinic, tartaric, cinnamic, benzoic, gluconic, ascorbic, salicyclic, ethane disulfonic, fumaric, glycolic, and related acids.

The compounds of the present invention possess valuable pharmacological properties. They are, for example, potent antidiarrheal agents. They are also capable of counteracting withdrawal symptoms of certain substances which produce chronic drug addiction. Additionally, the compounds of this invention variously possess analgesic, anti-protozoal, anti-bacterial, antifungal and anthelmintic activity.

The antidiarrheal properties of the instant compounds are specifically illustrated by the activity of the respective species N-[1-(3-cyano-3,3-diphenylpropyl)-4-phenylpiperidine-4-carbonyloxy]succinimide hydrochloride and 3-[1-(3-cyano-3,3-diphenylpropyl)-4-phenylpiperidine-4-carbonyloxy]-3H-1,2,3-benzotriazin-4-one hydrochloride in the following test procedures.

Charcoal Meal Test

Mice weighing 18-24 grams and previously fasted for 18 hours were each given orally 0.3 ml. of a suspension containing 10% charcoal and 5% acacia. The test compounds were administered intragastrically one hour prior to the charcoal meal. One-half hour after administration of the meal the mice were sacrificed with ether and their gastrointestinal tracts were removed. The distance over which some of the charcoal meal has moved from the pylorus to the cecum was measured for each mouse and expressed as percentage of the total distance. Each compound was tested at three dose levels (typically, at 0.3, 0.6 and 1.2 mg/mouse) in groups of 5 mice per dose level. Control groups of mice given saline only were run concurrently with each test group.

Castor Oil-Induced Diarrhea Test

Male Charles River rats were fasted overnight and water given ad lib. Test compounds (0.1 mg./kg.) were administered orally in normal saline, while controls were given saline only. The rats were randomized into two treatment groups and one control group, each group containing 10 rats. One hour after compound administration, 1 ml. of castor oil was given to each rat intragastrically. The rats were then observed for the presence or absence of diarrhea one hour after administration of the castor oil.

Indicative of the ability of the instant compounds to counteract withdrawal symptoms of certain substances which produce drug addiction is the active response observed when a representative species of this invention, N-[1-(3-cyano-3,3-diphenylpropyl)-4-phenylpiperidine-4-carbonyloxy]succinimide hydrochloride, was tested in the procedure described below for determining the ability of a compound to block the withdrawal jumping syndrome in mice. This procedure is a modification of that described by F. Huidobro et al. in Acta. Physiol. Latinoamer., 11, 70 and 201 (1961), Arch. Int. Pharmacodyn. Ther., 158, 97 (1965), and E. L. Way et al. in Science, 162, 1290 (1968) and J.P.E.T., 167 (1), 1 (1969).

On each day, for nine consecutive days, two groups of ten male albino mice are each given three morphine injections intraperitoneally at 6:30 A.M., 2:30 P.M. and 10:30 P.M. The initial dose is 4 milligrams per kilogram and each succeeding dose increases by 4 mg./kg. (E.g., Day 2 — 6:30 A.M. = 16 mg./kg., etc., through the 10:30 P.M. injection on the ninth day which brings the final dose up to 108 mg./kg.) On the morning of the 10th day, to one group of mice is administered a selected dose of the test compound, instead of the next morphine dose. In like manner the control group i.e. a group treated identically save for the lack of administration of test compound, are given saline solution by intragastric administration. Both groups of mice are then observed during the course of the day for vertical jumping of over eight inches which demonstrates the presence of the addiction withdrawal syndrome and the following activities are recorded:

1. Number of jumps for each hour of withdrawal observed,
2. Total jumps for the duration of the observed period, and
3. Number of mice jumping per group.

A test compound is considered to have withdrawal blocking properties i.e. to demonstrate an active response, if at some non-toxic dose it produces no withdrawal jumps on this regimen and if at other lower doses it causes reduced withdrawal jumping in a dose response way, i.e. — significantly less jumps than control animals or significantly fewer numbers of animals observed to jump than control animals with doses being administered at lower and lower levels until no significant differences exist between the control group and those administered the test compound.

The novel compounds of this invention can be combined with pharmaceutically acceptable carriers to provide novel pharmaceutical compositions. The concentration of active ingredient in the composition is not critical, but is preferably 1–80 percent. These compositions can be administered orally, suitable forms for such administration including tablets, lozenges, capsules, dragees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose of cellulose acetate phthalate; gelatin; talc; calcium phosphates such as dicalcium phosphate or tricalcium phosphate; sodium sulfate; calcium sulfate; polyvinyl pyrrolidone; acacia; polyvinyl alcohol; stearic acid; alkaline earth metal stearates such as magnesium stearate; oils such as peanut oil, cottonseed oil, sesame oil; olive oil, corn oil, oil of theobroma; water; agar; alginic acid; and benzyl alcohol, as well as other non-toxic compatible substances used in pharmaceutical formulations.

The compounds of this invention can be used to produce an antidiarrheal effect in mammals by administering the instant novel compositions containing a therapeutically effective amount of the active ingredient. The term "therapeutically effective amount" is defined as the amount of active ingredient that will produce an antidiarrheal effect, i.e. which will reverse, inhibit or prevent diarrhea. For a particular subject, the amount of active ingredient to be used will vary with the subject involved, the severity of the diarrhea, and the particular active ingredient used. The therapeutically effective amount of a particular active ingredient can be determined by comparing its potency to that of a known standard, for which the therapeutic dosage is known.

Those skilled in the art will recognize that observations of activity in standardized tests for particular biological effects are fundamental to the development of valuable new drugs, both veterinary and human.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade (°C).

EXAMPLE 1

N-[1-(3-cyano-3,3-diphenylpropyl)-4-phenylpiperidine-4-carbonyloxy]succinimide 24.5 Grams of 1-(3-cyano-3,3-diphenylpropyl)-4-phenylpiperidine-4-carboxylic acid are dissolved in 225 ml. of redistilled N,N-dimethylformamide by warming to about 60°C. To the warm solution were added, with stirring, 9.0 grams of recrystallized N-hydroxysuccinimide, followed by 12.4 grams of dicyclohexylcarbodiimide. A precipitate appears upon cooling to room temperature. The suspension is stirred at room temperature under anhydrous conditions for about 36 hours, then is cooled to approximately 5°C. and is filtered to remove the precipitate. The filtrate is diluted with approximately 400 ml. of ethyl acetate and 200 ml. of water. The organic layer is then separated and washed three times with water, solid sodium chloride being added as needed to break the emulsion formed. The solution is dried over anhydrous sodium sulfate and partially concentrated until a precipitate forms. Filtration and recrystallization of the precipitate from a mixture of tetrahydrofuran and isopropyl ether affords N-[1-(3-cyano-3,3-diphenylpropyl)-4-phenylpiperidine-4-carbonyloxy]succinimide, melting at about 156.5°–157.5°C. This product has the formula

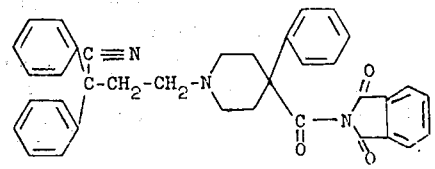

The ethyl acetate filtrate is acidified with concentrated hydrochloric acid in 2-propanol, diluted with ethyl ether to the point of incipient precipitation and cooled. The precipitate is filtered, recrystallized from a mixture of 2-propanol and isopropyl ether, and dried at about 110°C. under reduced pressure for about 16 hours. There is thus obtained N-[1-(3-cyano-3,3-diphenylpropyl)-4-phenylpiperidine-4-carbonyloxy]-succinimide hydrochloride which melts at about 242°–244°C. with gas evolution.

1.35 Grams of N-[1-(3-cyano-3,3-diphenylpropyl)-4-phenylpiperidine-4-carbonyloxy]succinimide are dissolved in 20 ml. of dichloromethane and then combined with a solution of 0.37 gram of glycolic acid in 10 ml. of warm dichloromethane. The resultant solution is filtered and diluted with ether and the semisolid thus obtained is dried to a solid in vacuo. The product, N-[1-(3-cyano-3,3-diphenylpropyl)-4-phenylpiperidine-4-carbonyloxy]succinimide hemihydrate, compound with 2 moles of glycolic acid, displayed a melting point at about 80°–85°C. with decomposition.

EXAMPLE 2

N-[1-(3-cyano-3,3-diphenylpropyl)-4-phenylpiperidine-4-carbonyloxy]phthalimide 2.12 Grams of 1-(3-cyano-3,3-diphenylpropyl)-4-phenylpiperidine-4-carboxylic acid are dissolved in 65 ml. of redistilled N,N-dimethylformamide by warming to about 60°C. To the warm solution is added, with stirring, .82 gram of N-hydroxyphthalimide, followed by 1.16 grams of dicyclohexylcarbodiimide. The resultant mixture is stirred at room temperature under calcium chloride, then cooled and filtered. The filtrate is diluted with water and extracted with ethyl acetate. The ethyl acetate layer is washed with water, dried over potassium carbonate and partially concentrated until a precipitate forms. Filtration and repeated crystallizations of the precipitate from a mixture of chloroform and hexane affords N-[1-(3-cyano-3,3-diphenylpropyl)-4-phenylpiperidine-4-carbonyloxy]phthalimide, melting at about 156.5°–157.5°C. The product has the formula

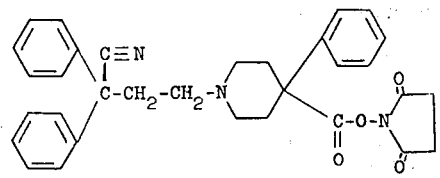

The ethyl acetate filtrate is acidified with concentrated hydrochloric acid in 2-propanol, diluted with isopropyl ether to the point of incipient precipitation and cooled. The precipitate is filtered, recrystallized from a mixture of 2-propanol and isopropanol ether and dried, thus affording N-[1-(3-cyano- 3,3-diphenylpropyl)-4-phenylpiperidine-4-carbonyloxy]phthalimide hydrochloride, compound with 2-propanol. That product melts at about 151°–153°C., with decomposition.

EXAMPLE 3

3-[1-(3-cyano-3,3-diphenylpropyl)-4-phenylpiperidine-4-carbonyloxy]-3H-1,2,3-benzotriazin-4-one-hydrochloride 2.12 Grams of 1-(3-cyano-3,3-diphenylpropyl)-4-phenylpiperidine-4-carboxylic acid are dissolved in 60 ml. of warm redistilled N,N-dimethylformamide. To that solution is then added .82 gram of 3-hydroxy-3H-1,2,3-benzotriazin-4-one, followed by 1.16 grams of dicyclohexylcarbodiimide. The resultant solution is stirred at room temperature under anhydrous conditions for about 24 hours, a precipitate appearing after approximately 1 hour. The suspension is cooled to about 5°C., the precipitate is removed by filtration, and the filtrate is diluted with 100 ml. of water and extracted twice with 100 ml. portions of ethyl acetate. The combined ethyl acetate layers are washed with water, dried, over anhydrous sodium sulfate, concentrated to approximately one-half volume by evaporation under a stream of nitrogen, and then filtered. The ethyl acetate solution is then acidified with concentrated hydrochloric acid in 2-propanol, diluted with ethyl ether and cooled. The precipitate which forms is recrystallized from a mixture of 2-propanol and isopropyl ether, then dried in vacuo at about 110°C. The product thus isolated is 3-[1-(3-cyano-3,3-diphenylpropyl)-4-phenylpiperidine- 4-carbonyloxy]-3H-1,2,3-benzotriazin-4-one hydrochloride, melting at about 208°–210°C. with decomposition, and having the formula

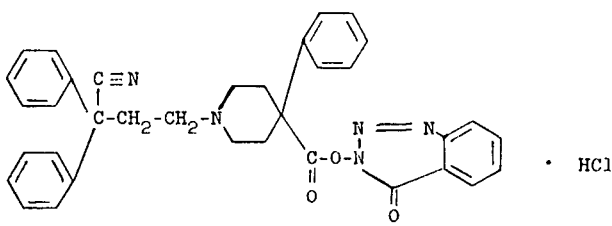

EXAMPLE 4

N-[1-(3-cyano-3,3-diphenylpropyl)-4-phenylpiperidine-4-carbonyloxy]-endo-5-norbornene-2,3-dicarboximide hydrochloride Substitution of .90 gram of N-hydroxy-endo-5-norbornene-2,3-dicarboximide for the 3-hydroxy-3H-1,2,3-benzotriazin-4-one used in Example 3 affords by substantial repetition of the there detailed procedure N-[1-(3-cyano-3,3-diphenylpropyl)-4-phenylpiperidine-4-carbonyloxy]-endo-5-norbornene-2,3-dicarboximide hydrochloride, compound with 2-propanol. The product foams at about 151°C. and has the formula

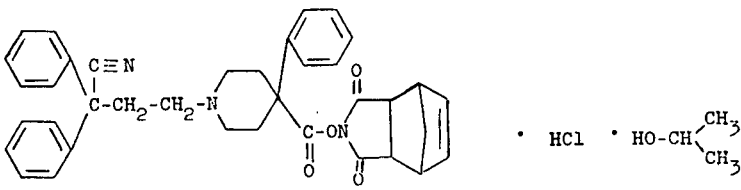

EXAMPLE 5

N-[1-(3-cyano-3,3-diphenylpropyl)-4-phenylpiperidine-4-carbonyloxy]glutarimide hydrochloride Substitution of .65 gram of N-hydroxyglutarimide for the 3-hydroxy-3H-1,2,3-benzotriazin-4-one used in Example 3 and substantial repetition of the procedure there detailed affords N-[1-(3-cyano-3,3-diphenylpropyl)-4-phenylpiperidine-4-carbonyloxy]glutarimide hydrochloride, melting at about 238°–244°C. with gas evolution, and having the formula

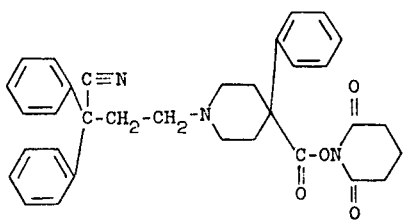

EXAMPLE 6

Hydrochloride salts of
4-[1-(3-cyano-3,3-diphenylpropyl)-4-phenylpiperidine-4-carbonyloxy]-2H-1,4-benzothiazin-3(4H)-one;
6-chloro-4-[1-(3-cyano-3,3-diphenylpropyl)-4-phenylpiperidine-4-carbonyloxy]-2-methyl-2H-1,4-benzoxazin-3(4H)-one;
1-[1-(3-cyano-3,3-diphenylpropyl)-4-phenylpiperidine-4-carbonyloxy]-2-indolinone; and
3-[1-(3-cyano-3,3-diphenylpropyl)-4-phenylpiperidine-4-carbonyloxy]-2-methylpyrido[3,2-d]-pyrimidin-4-one Substitution of equivalent .80 gram of 4-hydroxy-2H-1,4-benzoxazin-3(4H)-one; .90 gram of 1-hydroxy-2-indolinone, and .90 gram 3-hydroxy-2-methylpyrido[3,2-d] pyrimidin-4-one for the 3-hydroxy-3H-1,2,3-benzotriazin-4-one employed in Example 3 affords by substantial repetition of the procedure there described the hydrochloride salts of 4-[1-(3-cyano-3,3-diphenylpropyl)-4-phenylpiperidine-4-carbonyloxy]-2H-1,4-benzothiazin-3(4H)-one; 6-chloro-4-[1-(3-cyano-3,3-diphenylpropyl)-4-phenylpiperidine-4-carbonyloxy]-2-methyl-2H-1,4-benzoxazin-3(4H)-one; 1-[1-(3-cyano-3,3-diphenylpropyl)-4-phenylpiperidine-4-carbonyloxy]-2-indolinone; and 3-[1-(3-cyano-3,3-diphenylpropyl)-4-phenylpiperidine-4-carbonyloxy]-2-methylpyrido [3,2-d]-pyrimidin-4-one, respectively.

EXAMPLE 7

3-[1-(3-cyano-3,3-diphenylpropyl)-4-phenylpiperidine-4-carbonyloxy]-3H-quinazolin-4-one hydrochloride hemihydrate To a solution of 2.12 grams of 1-(3-cyano-3,3-diphenylpropyl)-4-phenylpiperidine-4-carboxylic acid in 60 ml. of warm redistilled N,N-dimethylformamide is added 0.81 gram of 3-hydroxy-3H-quinazolin-4-one, followed by 1.16 grams of dicyclohexylcarbodiimide. The resultant solution is stirred at room temperature under anhydrous conditions for about 24 hours, a precipitate appearing after approximately one hour. The suspension is cooled to about 5°C. and the precipitate is removed by filtration. The filtrate is diluted with water and extracted with ethyl acetate. The ethyl acetate solution is washed with water, dried over anhydrous sodium sulfate, concentrated to approximately one-half volume by evaporation under a stream of nitrogen, then filtered. The ethyl acetate solution is then acidified with concentrated hydrochloric acid in 2-propanol, diluted with isopropyl ether and cooled. The precipitate which forms is filtered and dried. There is thus obtained 3-[1-(3-cyano-3,3-diphenylpropyl)-4-phenylpiperidine-4-carbonyloxy]-3H-quinazolin-4-one hydrochloride hemihydrate, melting at about 237°–238.5°C., and having the formula

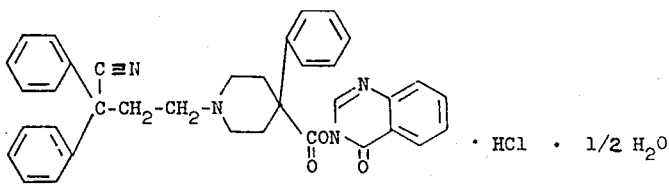

EXAMPLE 8

N-[1-(3-cyano-3,3-diphenylpropyl)-4-phenylpiperidine-4-carbonyloxy]phthalimide hydrochloride, compound with 2-propanol 2.12 Grams of 1-(3-cyano-3,3-diphenylpropyl)-4-phenylpiperidine-4-carboxylic acid are suspended in 10 ml. of dry tetrahydrofuran and 0.5–1.0 ml. of dry redistilled N,N-dimethylformamide. A solution of 5 ml. of thionyl chloride in 5 ml. of dry tetrahydrofuran is added dropwise, a clear solution resulting after the addition of about 2 drops. The resulting solution is stirred at room temperature under anhydrous conditions for about 5 minutes, then refluxed for 15 minutes. The reaction mixture is concentrated to a solid residue and excess thionyl chloride is further removed by adding 10 ml. of dry tetrahydrofuran and again concentrating to dryness. The residue, i.e. 1-(3-cyano-3,3-diphenylpropyl)-4-phenylpiperidine-4-carboxylic acid chloride hydrochloride, is taken up in 15 ml. of dry N,N-dimethylformamide, treated with 1 gram of triethylamine, then with .82 gram of N-hydroxyphthalimide in 5 ml. of N,N-dimethylformamide. The reaction mixture is stirred at room temperature for about 2 hours, then diluted with 50 ml. of water and extracted twice with 50 ml. portions of ethyl acetate. The combined ethyl acetate solutions are washed with water, dried and acidified with concentrated hydrochloric acid in 2-propanol. Addition of isopropyl ether and cooling affords a precipitate which is recrystallized from a mixture of 2-propanol and isopropyl ether containing decolorizing carbon. There is thus obtained N-[1-(3-cyano-3,3-diphenylpropyl)-4-phenylpiperidine-4-carbonyloxy]phthalimide hydrochloride, compound with 2-propanol, melting at about 151°–155°C. with gas evolution, and having the formula

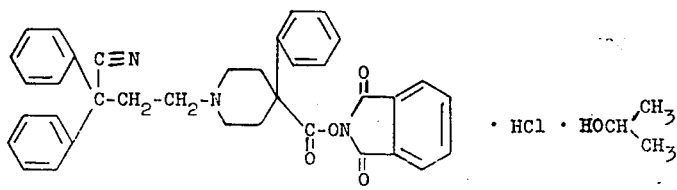

EXAMPLE 9

1-(3-cyano-3,3-diphenylpropyl)-4-phenylpiperidine-4-carboxylic acid chloride hydrochloride To 7 grams of 1-(3-cyano-3,3-diphenylpropyl)-4-phenylpiperidine-4-carboxylic acid suspended in 100 ml. of anhydrous tetrahydrofuran and 5 ml. of redistilled N,N-dimethylformamide is added 8 ml. of thionyl chloride in 50 ml. of anhydrous tetrahydrofuran. The resulting clear solution is stirred at room temperature under anhydrous conditions for about 5 minutes, then heated at the reflux temperature for 15 minutes and concentrated to dryness. To the residue is added an equal volume of tetrahydrofuran and the resultant mixture is contacted with a stream of nitrogen and stripped of solvent by vacuum distillation. The residue is triturated with cold tetrahydrofuran, then filtered. The filtrate is concentrated to dryness at room temperature in a nitrogen atmosphere. The solid residue is filtered with anhydrous ether and dried at room temperature in vacuo, thus affording 1-(3-cyano-3,3-diphenylpropyl)-4-phenylpiperidine-4-carboxylic acid chloride hydrochloride, melting at about 169°–171°C. with decomposition. The product has the formula

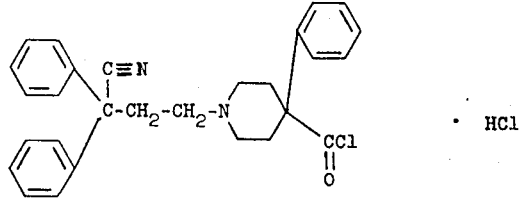

EXAMPLE 10

2.5 Milligram Tablets 2.5 Grams of a representative compound, e.g. N-1-(3-cyano-3,3-diphenylpropyl)-4-phenylpiperidine-4-carbonyloxy succinimide hydrochloride or 3-[1-(3-cyano-3,3-diphenylpropyl)-4-phenylpiperidine-4-carbonyloxy]-3H-1,2,3-benzotriazin-4-one hydrochloride, are mixed with 37.19 grams of powdered sucrose and 22.05 grams of corn starch, then screened and remixed. The mixture is granulated with 0.63 gram of polyvinylpyrrolidone in ethanol, then is dried and screened. 0.63 Gram of magnesium stearate is added and the product is remixed and compressed into tablets of the appropriate size. There is thus obtained a batch of 1000 tablets having a concentration of active ingredient of 2.5 mg./tablet.

When the above procedure is repeated utilizing 2.5 grams of the active ingredient premixed with 25 mg. of atropine sulfate, 37.165 grams of powdered sucrose, 22.05 grams of corn starch, 0.63 gram of polyvinylpyrrolidone and 0.63 gram of magnesium stearate, there is obtained a batch of 1000 tablets having a concentration of 2.5 mg. of active ingredient and .025 mg. of atropine sulfate per tablet.

EXAMPLE 11

1.0 Milligram Tablets

When the procedure of Example 10 is repeated using 1 gram of the active ingredient, 38.69 grams of powdered sucrose, 22.05 grams of corn starch, 0.63 gram of polyvinylpyrrolidone and 0.63 gram of magnesium stearate, there was obtained a batch of 1000 tablets having a concentration of active ingredient of 1.0 mg./tablet.

EXAMPLE 12

1.0 and 2.5 Milligram Capsules 1.0 Gram of a representative compound, e.g. N-[1-(3-cyano-3,3-diphenylpropyl)4-phenylpiperidine-4-carbonyloxy]succinimide hydrochloride or 3-[1-(cyano-3,3-diphenylpropyl)-4-phenylpiperidine-4-carbonylocy[-3H-1,2,3-benzotriazin-4-one hydrochloride, and 249 grams of corn starch are mixed, screened, remixed and filled into No. 2 hard gelatin capsules by hand or machine using 250 mg. fill per capsule. There is thus obtained a batch of 1000 capsules having a concentration of active ingredient of 1.0 mg./capsule.

Repetition of the above procedure using 2.5 grams of the active ingredient and 247.5 grams of corn starch afforded a batch of 1000 capsules having a concentration of active ingredient of 2.5 mg./capsule.

EXAMPLE 13

Liquids Having Concentrations of 1 mg./5cc and 2.5 mg./5cc

200 Mg. of a representative compound, e.g. N-[1-(3-cyano-3,3-diphenylpropyl)-4-phenylpiperidine-4-carbonyloxy]succinimide hydrochloride or 3-[1-(3-cyano-3,3-diphenylpropyl)-4-phenylpiperidine-4-carbonyloxy]-3H-1,2,3-benzotriazin-4-one hydrochloride, are dissolved in 165 ml. of alcohol. To the resultant solution is added 450 ml. of of glycerin. The mixture is stirred thoroughly while 1.0 ml. of cherry flavor and sufficient sorbitol solution to bring the total volume to 1000 ml. are added. The pH was adjusted to 8.5 to 9.0 using sodium or potassium hydroxide solution and the liquid was filtered. There is thus obtained a liquid having a concentration of active ingredient of 1 mg./5cc.

When the above procedure is repeated using 500 mg. of the active ingredient, 175 ml. of alcohol, 450 ml. of glycerin, 1.5 ml. of cherry flavor and sufficient sorbitol solution to bring the total volume to 1000 ml., there is obtained a liquid having a concentration of active ingredient of 2.5 mg./5cc.

What is claimed is:

1. A compound which is 3-[1-(3-cyano-3,3-diphenylpropyl)-4-phenylpiperidine-4-carbonyloxy]-3H-1,2,3-benzotriazin-4-one and the hydrochloride salt thereof.

* * * * *